(12) United States Patent
Abe et al.

(10) Patent No.: US 7,944,209 B2
(45) Date of Patent: May 17, 2011

(54) MAGNETIC RESONANCE IMAGING APPARATUS AND METHOD

(75) Inventors: Takayuki Abe, Tokyo (JP); Tetsuhiko Takahashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 309 days.

(21) Appl. No.: 12/295,160

(22) PCT Filed: Mar. 12, 2007

(86) PCT No.: PCT/JP2007/054788
§ 371 (c)(1),
(2), (4) Date: Sep. 29, 2008

(87) PCT Pub. No.: WO2007/113992
PCT Pub. Date: Oct. 11, 2007

(65) Prior Publication Data
US 2010/0244823 A1    Sep. 30, 2010

(30) Foreign Application Priority Data
Mar. 31, 2006   (JP) ................... 2006-099567

(51) Int. Cl.
*G01V 3/00*    (2006.01)

(52) U.S. Cl. ........................ 324/309; 324/312
(58) Field of Classification Search .......... 324/309, 324/312
See application file for complete search history.

(56) References Cited

U.S. PATENT DOCUMENTS

| | | | |
|---|---|---|---|
| 6,445,182 B1 * | 9/2002 | Dean et al. | 324/309 |
| 7,417,430 B2 * | 8/2008 | Aldefeld et al. | 324/309 |
| 7,535,227 B1 * | 5/2009 | Koch et al. | 324/309 |

FOREIGN PATENT DOCUMENTS

| | | |
|---|---|---|
| JP | 61-172550 | 8/1986 |
| JP | 1-107749 | 4/1989 |
| JP | 4-208133 | 7/1992 |
| JP | 8-191820 | 7/1996 |

* cited by examiner

*Primary Examiner* — Louis M Arana
(74) *Attorney, Agent, or Firm* — Cooper & Dunham LLP (57) ABSTRACT

A magnetic resonance imaging apparatus is configured to generate a correcting magnetic field for correcting a static magnetic field, based on a first set of information representing an inhomogeneous distribution of the static magnetic field generated depending on the characteristic of the static magnetic field generating means, a second set of information representing an inhomogeneous distribution of the static magnetic field generated depending on the tissue of the object, a third set of information corresponding to a set field of view for imaging in a desired region of the object.

20 Claims, 9 Drawing Sheets

MAGNETIC RESONANCE IMAGING APPARATUS AND METHOD

TECHNICAL FIELD

The present invention is related to a magnetic resonance imaging (hereinafter referred to as MRI) apparatus and method, particularly to a technique capable of improving correction of inhomogeneous distribution of the static magnetic field in a method for imaging a wide range of region while moving a table.

BACKGROUND ART

An MRI apparatus is, when electromagnetic waves are irradiated to an object to be examined placed in a homogeneous static magnetic field, for obtaining a magnetic resonance image (hereinafter referred to as MRI) that represents the physical description of the object by detecting a nuclear magnetic resonance signal (hereinafter referred to as an NMR signal) using NMR phenomenon generated in atomic nuclei of an atom by which the object is constituted and reconstructing an image using the NMR signal.

In MRI, a technique is commonly known for imaging a wide range or whole body of an object while moving a table on which the object is placed in a gantry of an MRI apparatus. In such technique there are the following two methods of moving the table. One is the multi-station imaging method that divides the wide range or the whole body range of the object into a plurality of blocks and performs imaging for each block while moving the table stepwise (for example, refer to Patent Document 1). The other one is the moving table imaging method that images a wide range or a whole body range of the object at one time while continuously moving the table (for example, refer to Patent Document 2).

Patent Document 1: U.S. Pat. No. 6,311,085
Patent Document 2: JP-A-2004-611

Meanwhile, there is a technique called "shimming" for improving the quality of the images obtained by MRI. Shimming is a method for obtaining a high quality image by correcting the inhomogeneity of static magnetic field generated in an imaging space of in which an object is placed by applying the current to a shim coil whereby enabling to perform imaging in high uniformity condition of static magnetic field (for example, refer to Patent Document 3). Here, there are two kinds of inhomogeneous distribution of the static magnetic field that is a target of shimming: one is apparatus-inherent inhomogeneous distribution of the static magnetic field generated from MRI apparatuses (hereinafter referred to as apparatus-inherent inhomogeneous distribution of the static magnetic field), and the other one is inhomogeneous distribution of the static magnetic field generated inside of the object because every tissue of the object has slightly different magnetic permeability when the object is placed inside of MRI apparatus (hereinafter referred to as object-dependent inhomogeneous distribution of the static magnetic field).

Patent Document 3: JP-A-H11-113880

As a result of studying the above conventional technique, the present inventors found the problems below. That is, when the above-mentioned table is moved continuously or stepwise while imaging, NMR signals are collected while the table is placed in various positions. In this case, in order to obtain high-quality images by the above-described shimming process, many steps are required since inhomogeneity of static magnetic field must be measured for each table position, whereby consuming a long time for measurement.

BRIEF SUMMARY

In an aspect of this disclosure, there are provided, in a context of imaging a wide range of an object while moving a table, an MRI apparatus and method capable of easily calculating inhomogeneous distribution of the static magnetic field generated when an arbitrary region of the object is placed in an imaging space.

The In another aspect of this disclosure, there is provided an MRI apparatus that comprises:
   static magnetic field generating means for generating a static magnetic field in an imaging space;
   measuring means for generating a high-frequency magnetic field and a gradient magnetic field in the imaging space, and measuring a nuclear magnetic resonance signal produced from the object placed in the imaging space;
   signal processing means for reconstructing a magnetic resonance image based on the nuclear magnetic resonance signal;
   control means for controlling the measuring means and the signal processing means; and
   display means for displaying the magnetic resonance image obtained by the signal processing means,
   characterized in further comprising:
   storing means for storing a set of first information representing inhomogeneous distribution of the static magnetic field generated depending on the characteristic of the static magnetic field generating means and a second set of information representing inhomogeneous distribution of the static magnetic field generated depending on a tissue in the object;
   setting means for setting imaging FOV in a desired region of the object;
   selecting means, from among the second set of information, for selecting the information corresponding to the set imaging FOV as a third set of information; and
   correcting magnetic field generating means for generating a correcting magnetic field for correcting the static magnetic field based on the third set of information and the first set of information.

In another aspect of this disclosure, there is provided an MRI method for obtaining a magnetic resonance image which comprises:
   (1) a step for setting an imaging FOV that represents a desired region of the object;
   (2) a step for selecting, from among the second set of information, the information corresponding to the set imaging FOV as the third set of information;
   (3) a step for acquiring the fourth set of information by adding the third set of information and the first set of information; and
   (4) a step for applying a high-frequency magnetic field and a gradient magnetic field to the object placed in the imaging space while generating a correcting magnetic field based on the fourth set of information, and measuring the nuclear magnetic resonance signal generated thereby.

BRIEF DESCRIPTION OF THE DIAGRAMS

THE BEST MODE FOR CARRYING OUT THE INVENTION

Figure 1:
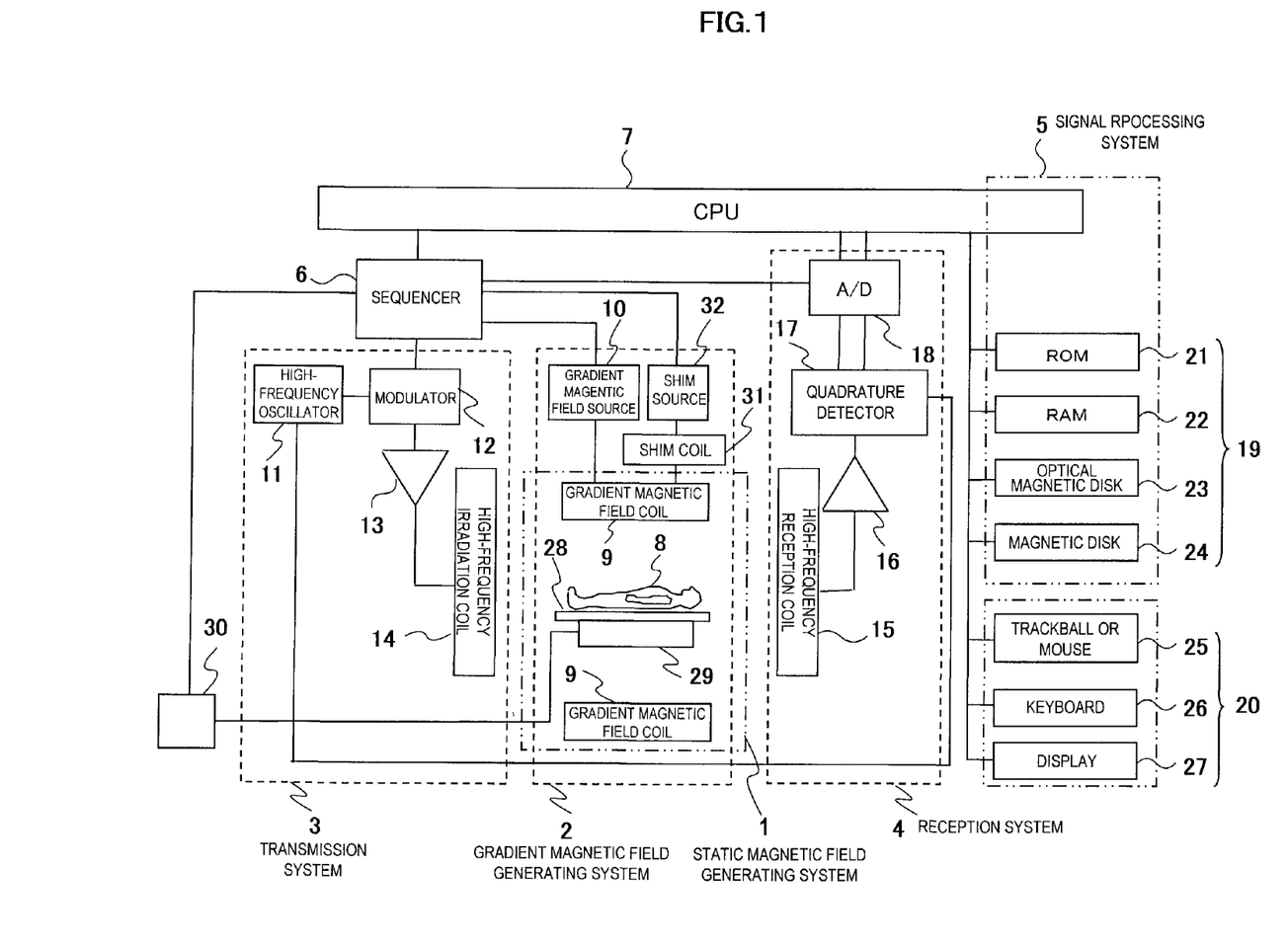
FIG. 1 is a block diagram showing the general configuration of the MRI apparatus related to the present invention.

FIG. 1 is a block diagram showing the general configuration of the MRI apparatus related to the present invention. The MRI apparatus thereof mainly comprises a static magnetic field generating system 1, a gradient magnetic field generating system 2, a transmission system 3, a reception system 4, a signal processing system 5 and a control system (a sequencer 6 and a CPU 7) as shown in FIG. 1.

The static magnetic field generating system 1 is for generating a homogeneous static magnetic field in a space around an object 8 (imaging space), and is configured by a magnetic device using a method such as a permanent magnetic method, normal conducting method or superconducting method.

The gradient magnetic field system 2 comprises, for example, when the direction of a gradient magnetic field is set as Z-direction and the two directions which are orthogonal thereto are set as X-direction and Y-direction, three gradient magnetic field coils 9 for generating a gradient magnetic field pulse to the three axis directions thereof, and a gradient magnetic field source 10 for driving them respectively. By driving the gradient magnetic field source 10, it is possible to generate a gradient magnetic field pulse in the direction of X, Y and Z or to a combination of the directions thereof. The gradient magnetic field pulse is applied in order to specify the imaging position of the object 8, and to append positional information to the NMR signal generated from the object 8.

The transmission system 3 comprises a high-frequency oscillator 11, a modulator 12, a high-frequency amplifier 13 and a high-frequency irradiation coil 14 for transmission. The electromagnetic wave (high-frequency signal, RF pulse) for causing an atomic nuclei of an atomic element that configures the body of an object to generate nuclear magnetic resonance is irradiated to the object by modulating an RF pulse generated by the high-frequency oscillator 11 to a signal of a predetermined envelope by the modulator 12, amplifying the signal in the high-frequency amplifier 13 and applying it to the high-frequency irradiation coil 14. The high-frequency irradiation coil 14 is usually placed in the vicinity of the object.

The reception system 4 comprises a high-frequency reception coil 14 for reception, an amplifier 16, a quadrature detector 17 and an A/D converter 18. The NMR signal generated from the object as a response to the RF pulse irradiated from the high-frequency irradiation coil 14 for transmission is detected by the high-frequency reception coil 15 for reception, amplified by the amplifier 16, converted into digital quantity by the A/D converter 18 via the quadrature detector 17, and transmitted to the signal processing system 5 as two series of collection data.

The signal processing system 5 comprises the CPU 7, a storage device 19 and an operation unit 20, and performs a variety of signal processing such as Fourier transformation, calculation of correction coefficient and image reconstruction to the digital signal received by the reception system 4 in the CPU 7. The storing device 19 comprises a ROM 21, a RAM 22, an optical magnetic disk 23, a magnetic disk 24, etc. and for example, stores a program for performing time course of image analysis processing and measurement or invariant parameter to be used for the execution of the program thereof to the ROM 21, measurement parameter obtained from overall measurement or echo signals detected in the reception system, etc. to the RAM 22, and the reconstructed image data to the optical disk 23 or the magnetic disk 24 respectively. The operating unit 20 comprises input means such as a trackball or a mouse 25, a keyboard 26 and a display 27 for displaying GUI necessary for input and the processing result of the performance in the signal processing system 5, etc. The information necessary for various processing or control to be executed by the CPU 7 is inputted via the operation unit 20. Also, the images obtained by imaging are displayed on the display 27.

The control system comprises the sequencer 6 and the CPU 7, and controls the operation of the above-described gradient magnetic generating system 2, the transmission system 3, the reception system 4 and the signal processing system 5. Especially, application timing of the gradient magnetic pulse and the RF pulse generated by the gradient magnetic field generating system 2 and the transmission system 3 and acquisition timing of the echo signal by the reception system 4 are controlled by a predetermined pulse sequence determined by the imaging method via the sequencer 6.

Embodiment 1

Next, the MRI apparatus and method of the embodiment 1 will be described in concrete form.

The MRI apparatus related to the embodiment 1 of the present embodiment in FIG. 1 further comprises a table control system. The table control system comprises a table 28 on which an object is placed, a table moving mechanism 29 which is installed parallel to the table 28 for moving the table 28 in the respective 3-dimensional directions, and a table control unit 30 for controlling the table movement in connection with the pulse sequence by the control of the sequencer 6 or the CPU 7. The table moving mechanism 29 is connected to the table control unit 30, and the table control unit 30 is connected to the sequencer 6. Also, the table moving mechanism 29 comprises a position detecting unit (not shown in the diagram) for detecting the position of the table 28. The table control unit 30 controls the movement of the table 28 using the positional information from the position detecting unit thereof and provides information such as the correction quantity necessary for the correction of the MR signals to the signal processing system 5.

Further, the MRI apparatus related to the embodiment 1 of the present invention comprises the gradient magnetic generating system 2 provided with a shim coil 31 for correcting noninformity of the static magnetic field and a shim source 32 for providing current to the shim coil 31. The shim coil 31 is connected to the shim source 32. The shim coil 31 is constituted by combining low-order and high-order coils and is made multi-channel. As for the coils that generate the correction magnetic field of the first-order term, the gradient magnetic field coil 9 may combine the function of the shim coil. Variation of the static magnetic field distribution (feature of the shim coil) generated by the respective shim coils 31 is measured in advance as the apparatus-inherent value, and is to be used upon calculating the shim current value in the shimming process.

Figure 2:
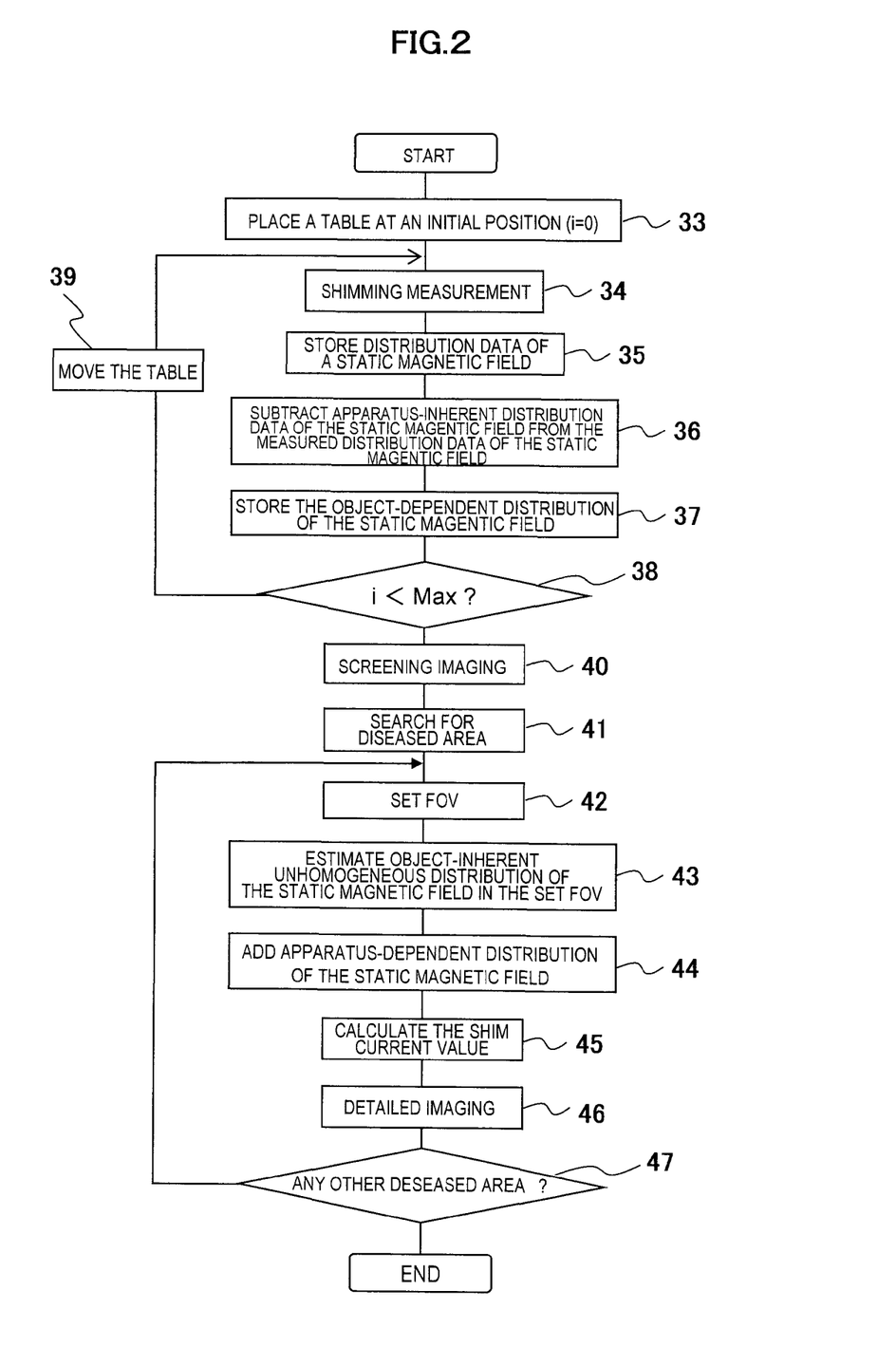
FIG. 2 is a flow chart illustrating the operation of embodiment 1 of the MRI apparatus related to the present invention.
Figure 3:
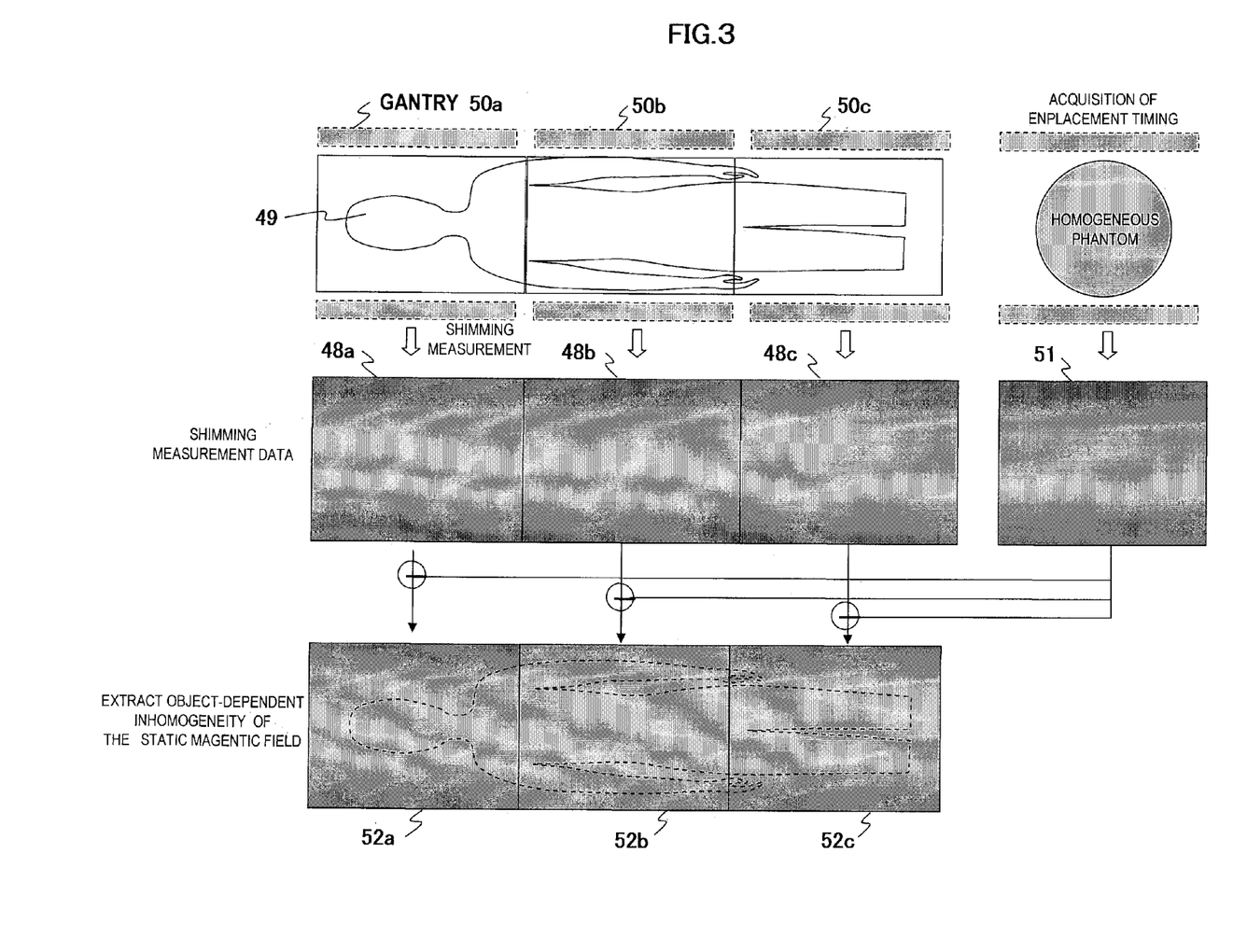
FIG. 3 is a schematic diagram of the shimming measurement in the embodiment 1.
Figure 4:
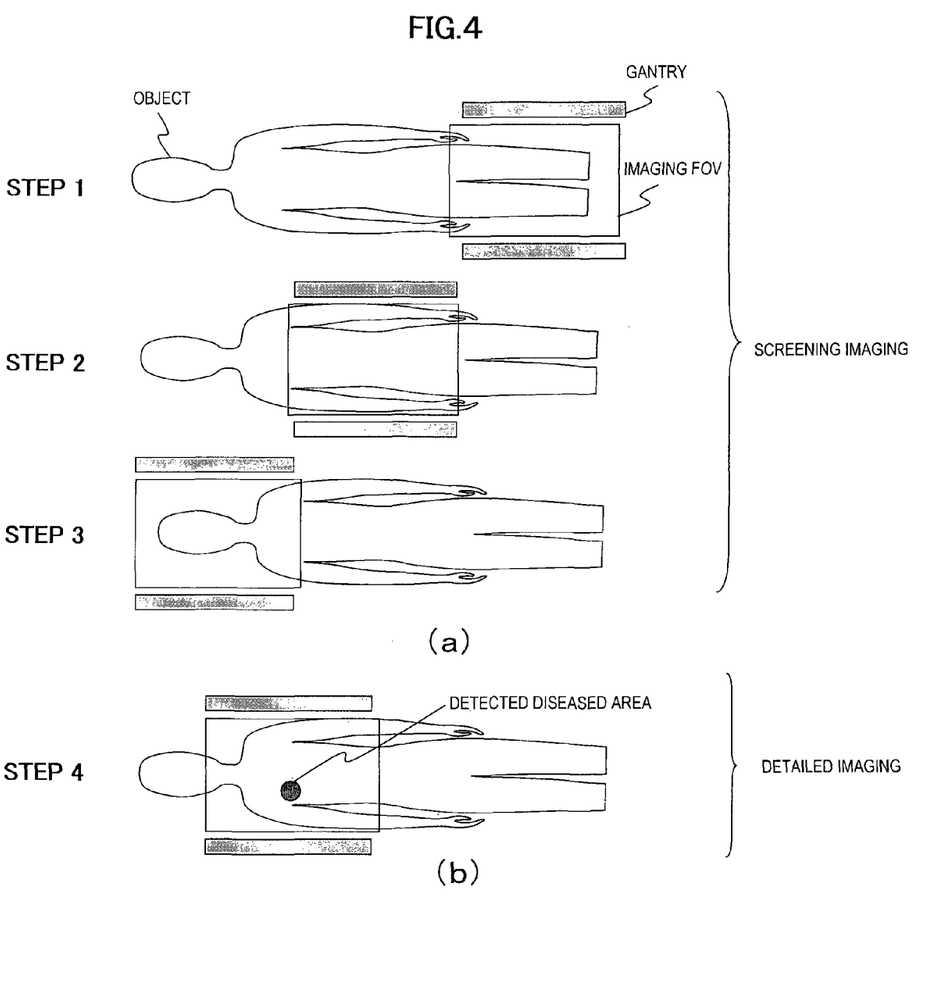
FIG. 4 is a schematic diagram on setting the FOV for an imaging for screening and detailed imaging in the embodiment 1.
Figure 5:
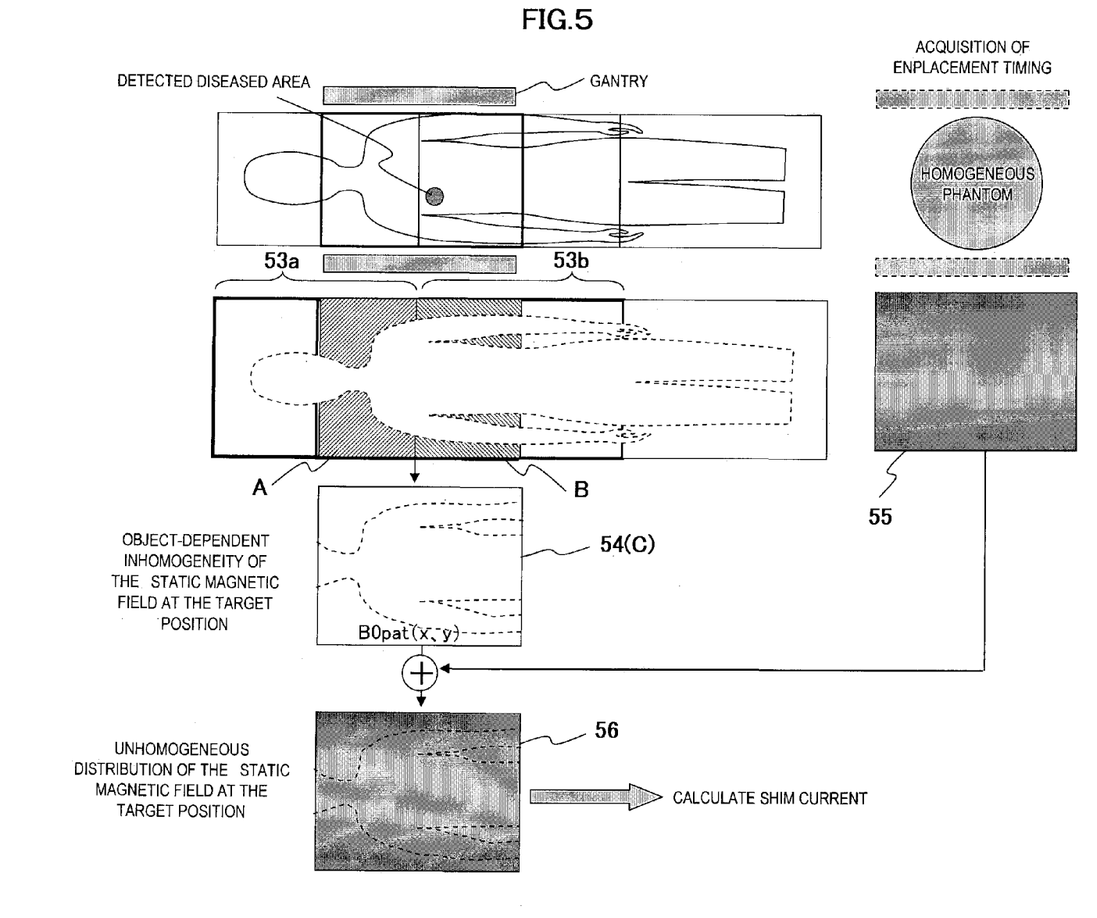
FIG. 5 is a schematic diagram representing the procedure from acquisition of inhomogeneous distribution of the static magnetic field in the set FOV to calculation of current value for the shim coil.

Next, the operation of the MRI apparatus related to the embodiment 1 of the present invention will be described. FIG. 2 is a flow chart showing the operation of the embodiment 1 of the MRI apparatus related to the present invention. FIG. 3 is a schematic diagram showing the shimming measurement in the embodiment 1. FIG. 4 is a schematic diagram showing the process for setting the field of view for an imaging for screening and detailed imaging in the embodiment 1. FIG. 5 is a schematic diagram showing the process of obtaining the inhomogeneous distribution of a static magnetic field in the set FOV and calculating the current value to be provided to the shim coil. The operation of the MRI apparatus thereof can be roughly divided into steps (hereinafter referred to as shimming measurement) 33~39 for obtaining the inhomogeneous distribution of the static magnetic field for shimming (data of spatial distribution) and steps 40~47 for obtaining image data of an object (real imaging). In the real imaging, dynamic shimming (correction of a magnetic field) is executed using the result of inhomogeneous distribution of the static magnetic field obtained by the steps 33~39. Hereinafter, each step will be described in order.

(Step 33)
The table 28 is placed at an initial position and a counter related to the position of the table is set at zero.

(Step 34)
Shimming measurement is performed in the respective positions of the table (hereinafter referred to as the respective station positions). The shimming measurement is performed by any of the measurement methods for measuring distribution of the static magnetic field that are commonly known. In concrete terms, a method may be used such as (a) a method for measuring from the spatial distribution of the phasing information included in the echo signals acquired by reversing the gradient magnetic field pulse, (b) a method for detecting the spectrum of a specific element using the chemical shift imaging method and measuring the spatial distribution of the frequency difference of the spectrum thereof, and (c) a method for measuring spatial distribution of the phase difference between two imaging data sets at different TE (echo times). For example, one of the methods for measuring the spatial distribution of the phase difference between two imaging data sets at different TE (echo times) is disclosed in "Rapid in Vivo Proton Shimming", MAGNETIC RESONANCE IN MEDICINE 18, 335-347 (1991).

Also, the shimming measurement to be performed at each station position in the present step may be performed along with the survey scan to be performed in each allocation. The survey scan is an imaging (scanning), in the respective position stations, for performing the measurement to adjust the offset of the gradient magnetic field, the measurement for tuning the coil, the measurement of the central frequency, the measurement for adjusting the irradiation gain, etc.

(Step 35)
The distribution of the static magnetic field for every station measured in step 34 is stored (saved) in a memory in the signal processing system 5. The distribution shown in 48a~48c of FIG. 3 are the respective illustrations of the static magnetic field distribution measured in step 34 and stored in the memory in the present step. Each of 48a~48c shows inhomogeneous distribution of the static magnetic field in the case that a gantry is placed at each position of 50a~50c with respect to an object 49.

(Step 36)
The inhomogeneous distribution of the static magnetic field measured in step 35 includes the apparatus-inherent inhomogeneous distribution of the static magnetic field and the object-dependent inhomogeneous distribution of the static magnetic field. Therefore, the object-dependent inhomogeneous distribution of the static magnetic field at each station position is obtained by subtracting the apparatus-inherent inhomogeneous distribution of the static magnetic field 51 from the inhomogeneous distribution of the respective stations stored in the memory in step 35. Apparatus-inherent inhomogeneous distribution is obtained in advance using a phantom, etc.

(Step 37)
The object-dependent inhomogeneous distribution of the static magnetic field obtained in step 36 is stored in the memory in the signal processing unit 5. The object-dependent inhomogeneous distribution of the static magnetic field obtained in step 36 and stored in the memory in step 37 is as illustrated in 52a~52c of FIG. 3.

(Step 38)
The determination is made whether the counter related to the table arrangement position reached the maximum value. If the value of the counter is lower than the maximum value, step 39 is to proceed. If the value reaches the maximum value, step 40 is to proceed.

(Step 39)
The table is moved to the next station position and the counter related to the table position is incremented by one. The object-dependent inhomogeneous distribution of the static magnetic field in the entire range of the object is obtained by repeatedly executing the above-mentioned steps 34~39.

(Step 40)
Next, the imaging for screening for the whole body is executed for the purpose of detecting the diseased area. In the imaging for screening, the imaging is executed in the respective stations by moving the table stepwise from head toward feet or from feet toward head. FIG. 4(a) is the schematic diagram illustrating the present step. Though shimming (correction of the static magnetic field) is not fundamental in the imaging thereof for screening, when shimming is to be executed, the current is applied to the shim coil upon imaging at the respective stations by calculating the shim current value in the respective stations based on the 48a~48c stored in the memory in the step 35.

(Step 41)
After the imaging for screening in the step 40, a diseased area is detected (traced) from the entire region of the object. The detection (tracing) here is executed by gross inspection or image processing.

(Step 42)
Hereinafter, preparation for detailed imaging of the diseased area screened in the step 41 is performed. First, the field of vision is set so as to position the diseased area for the detailed imaging at the center. The schematic diagram of setting FOV is shown in FIG. 4(b).

(Step 43)
Next, inhomogeneous distribution of the static magnetic field in the FOV set in the step 42 is estimated. The inhomogeneous distribution of the static magnetic field to be estimated in the present step is the addition of the apparatus-inherent inhomogeneous distribution of the static magnetic field and the object-dependent inhomogeneous distribution of the static magnetic field. Given this factor, first in the present step, the inhomogeneous distribution of the static magnetic field of the FOV set in the step 42 is selected from the object-dependent inhomogeneous distribution of the static magnetic field in the entire region of the object stored in the step 37. The schematic diagram of the procedure thereof is shown in FIG. 5. In concrete terms, the object-dependent inhomogeneous distribution of the static magnetic field in the imaging FOV of the diseased area shown in 54 (region C) is obtained by combining a part of the inhomogeneous distribution of the static magnetic field in the station position of 53*a* in FIG. 5 (the region placed on the head side of the object: region A) and a part of the inhomogeneous distribution of the static magnetic field in the station position of 53*b* of FIG. 5 (the region positioned on the head side of the object: region B).

(Step 44)

Next, the inhomogeneous distribution of the static magnetic field necessary upon imaging the FOV of the diseased area is calculated by adding the apparatus-inherent inhomogeneous distribution of the static magnetic field to the object-dependent inhomogeneous distribution of the static magnetic field in the imaging FOV of the diseased area obtained in the step 43. The apparatus-inherent inhomogeneous distribution of the static magnetic field is obtained in advance using a phantom, etc. The addition to be performed in the present step is equivalent to the addition of "54" and "55" to generate "56" in FIG. 5.

(Step 45)

Next, on the basis of inhomogeneous distribution of the static magnetic field necessary upon imaging the imaging FOV of a diseased area calculated in the step 44, the shim current value for generating the static magnetic field for canceling the inhomogeneous distribution thereof is calculated. A commonly known method can be applied to calculate the shim current value in the present step. For example, spatial distribution data is developed to spherical harmonics, a component of the term corresponding to the order of the shim coil provided to the apparatus (first-order term component, second-order term component, . . . ) is obtained and the current value for canceling the component of the respective order terms is calculated using the obtained components and characteristic of the shim coil in the respective order.

(Step 46)

The detailed imaging of the diseased area is executed while correcting the static magnetic field by applying the shim current value calculated in the step 45.

(Step 47)

In the case that there are a plurality of diseased areas detected in the step 41 and there are other areas where the detailed imaging has not been executed yet, the step returns to the step 42, repeats from the step 42 to the step 46 several times, and executes the detailed imaging on the respective diseased areas.

In accordance with the above embodiment, it is possible upon imaging any region of the object to easily execute calculation for correcting inhomogeneity of the static magnetic field and correction using the calculation result thereof by consistently corresponding to the respective regions of the object, without calculating the shimming measurement each time. It is also possible to execute imaging of high quality images while maintaining high uniformity of the static magnetic field. For example, preferable high quality images can be obtained in application where high uniformity of a static magnetic field is required such as the EPI imaging, fat suppression imaging by frequency selection and spectroscopic imaging. The method in accordance with the present embodiment has an advantage to reduce measurement time for shimming measurement since there is no need to execute shimming measurement by corresponding to the respective regions of an object that are placed in an imaging space.

Even in the case that the station number of imaging for screening executed in prior to the detailed imaging is different from the station number of shimming measurement, the imaging for screening can be executed by properly executing shimming by calculating inhomogeneous distribution of the static magnetic field as described above for each station of the imaging for screening.

Also, accuracy of shimming in the above-described embodiment is limited by order of the shim coil provided to the apparatus. For example, the shimming of high-order magnetic component cannot be executed when the order of the shim coil is arranged up to the second order coil. Preferable images can be obtained if inhomogeneous distribution of the static magnetic field can be corrected up to the second order component in general applications, but there are cases that the correction up to high-order component is required in a part of the application. In such a case, degradation of image quality due to inhomogeneity of the static magnetic field can be further reduced by correcting the phase of the echo signal obtained by a detailed imaging using the technique disclosed in JP-A-2004-261591, etc. The technique disclosed in JP-A-2004-261591 has an advantage of being capable of reducing calculation amount for correction after acquisition of the signals since the low-order component of the magnetic field can be corrected in advance using a shim coil, by combining it with the above-described correction using a shim coil.

Also, while the above-described shimming measurement may be executed along with the survey scan in the step 34, it also may be executed along with the imaging for screening to be performed in the step 40.

Embodiment 2

Figure 6:
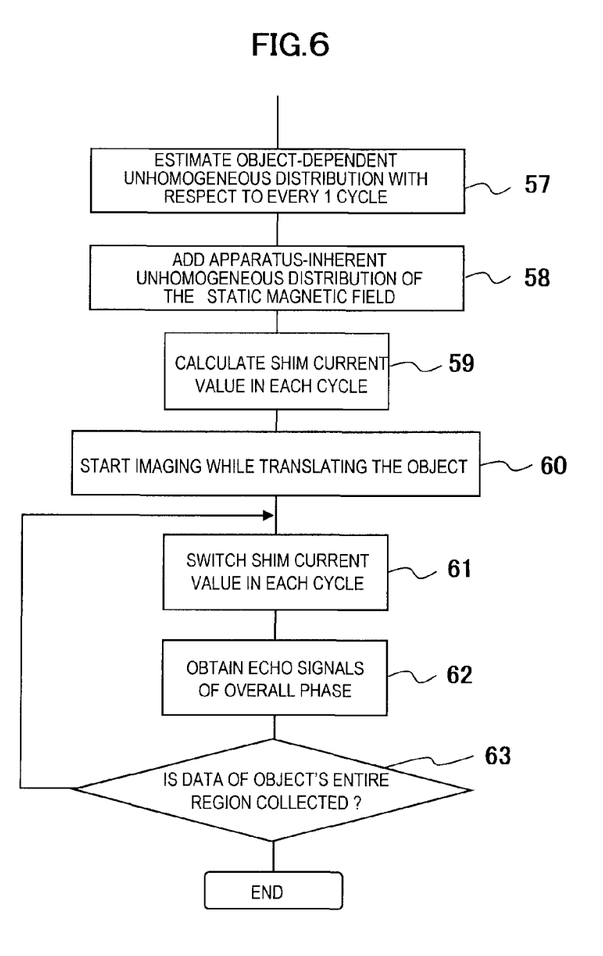
FIG. 6 is a flow chart of the operation in the second embodiment of the MRI apparatus related to the present invention.

Next, the concrete configuration of the MRI apparatus and method in embodiment 2 will be described. The present embodiment is an example of the case that the table is to be moved continuously. FIG. 6 is a flow chart showing the operation in the embodiment 2 of the MRI apparatus related to the present invention. In this embodiment, the steps of shimming measurement from step 33 to step 39 are the same as the embodiment 1, and only the steps of the present imaging are different.

Figure 7:
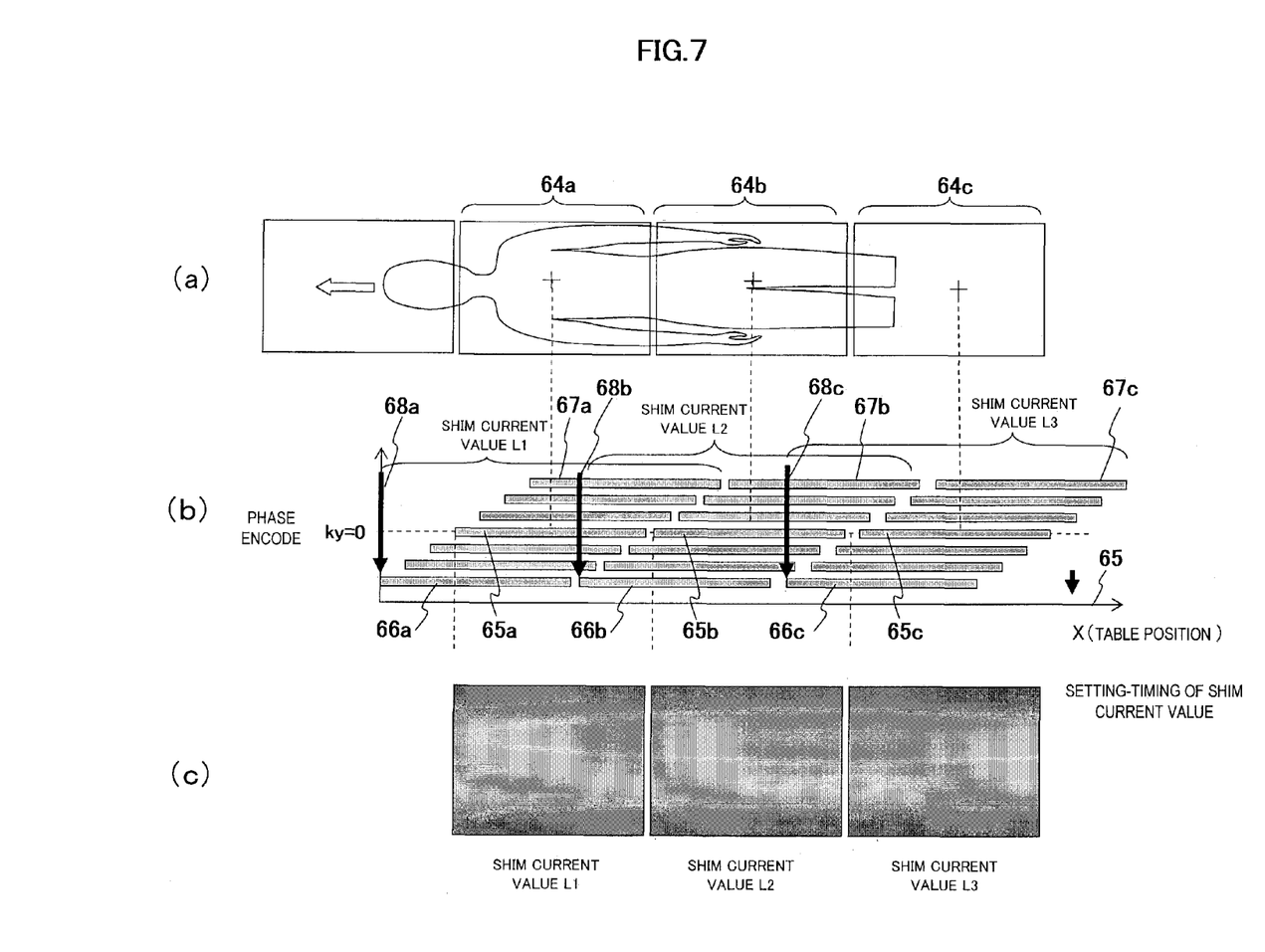
FIG. 7 is a schematic diagram of the imaging in the embodiment 2.

In the present embodiment, as shown in the schematic diagram of the imaging in FIG. 7, the imaging is executed while continuously moving the object with respect to the imaging FOV from the head part toward the feet. The imaging sequence used in the present imaging is arbitrarily determined in accordance with the objective of examination and not limited in any specific way. In the example shown in FIG. 7(*a*) of the present embodiment however, the direction for reading out the signals is the moving direction of the table, and the gradient magnetic field direction is selected so as to make the coronal cross-section as the imaging cross-section. In such imaging method, the position of the object changes for each detection of an echo signal. In the present embodiment, shimming is dynamically executed in accordance with such positional changes of the object. Concretely, acquisition of an echo signal by overall phase is set as one cycle, and shimming is executed for each cycle thereof. Steps of the present imaging in the present embodiment will be described below.

(Step 57)

Object-dependent inhomogeneous distribution of the static magnetic field is obtained for every 1 cycle of the echo signal acquisition with respect to an overall phase encode. In the present step, for example, the object-dependent inhomogeneous distribution of the static magnetic field with respect to the imaging FOV of the gantry placement when the phase encode amount is zero (such case that the imaging FOVs turn out as shown in 64a, 64b and 64c of FIG. 7(a)).

(Step 58)

Apparatus-inherent inhomogeneous distribution of the static magnetic field is added to the object-dependent inhomogeneous distribution of the static magnetic field obtained in the step 57. As a result, inhomogeneous distribution of the static magnetic field necessary for the actual imaging can be calculated with respect to the imaging FOV of the gantry allocation when the phase encode amount is zero.

(Step 59)

On the basis of the inhomogeneous distribution of the static magnetic field obtained by the step 58, the current value for applying to the shim coil is obtained in order to correct the inhomogeneity thereof.

(Step 60)

The imaging is to be started while continuously moving the object with respect to the gantry from the head-region toward the feet.

(Step 61)

With respect to every gantry allocation of a predetermined zone (allocation denoted by 66a~67a, 66b~67B and 66c~67c in FIG. 7(b)) centered on the gantry allocation when the phase encode amount is zero (for example, the allocation upon acquiring the echo denoted in FIG. 7(b) by 65a~65c on the coordinate wherein the bed position is set as the lateral axis and the phase encode is set as the vertical axis), the current obtained in the step 59 (denoted in FIG. 7 corresponded to the allocation respectively by L1, L2 and L3) is switched and applied to the shim coil. Concretely, the current value for applying to the shim coil is switched in the timing denoted by 68a~68c.

(Step 62)

The acquisition of the overall phase encode signal is repeated for a plurality of cycles while continuously moving the table.

(Step 63)

The operation is to be ended when the data collection for the entire range of the table movement is completed, and if the collection is not completed the operation is to be returned to the step 61.

In accordance with the above-described embodiment, in the moving-table imaging method wherein the position of the object continuously changes, highly accurate correction of the static magnetic field can be executed without breaking up the moving-table imaging, by updating the shim current value in accordance with the position of the object at a predetermined interval. In particular, the present embodiment is an example capable of obtaining the signal when the phase encode is zero by most effectively reducing the influence due to inhomogeneity of the static magnetic field.

In this regard, however, the timing for switching the current to apply to the shim coil in the present embodiment does not have to be limited to every 1 cycle, and may be each arbitrary echo number. For example, it may be switched with respect to every 1 echo.

Embodiment 3

Figure 8:
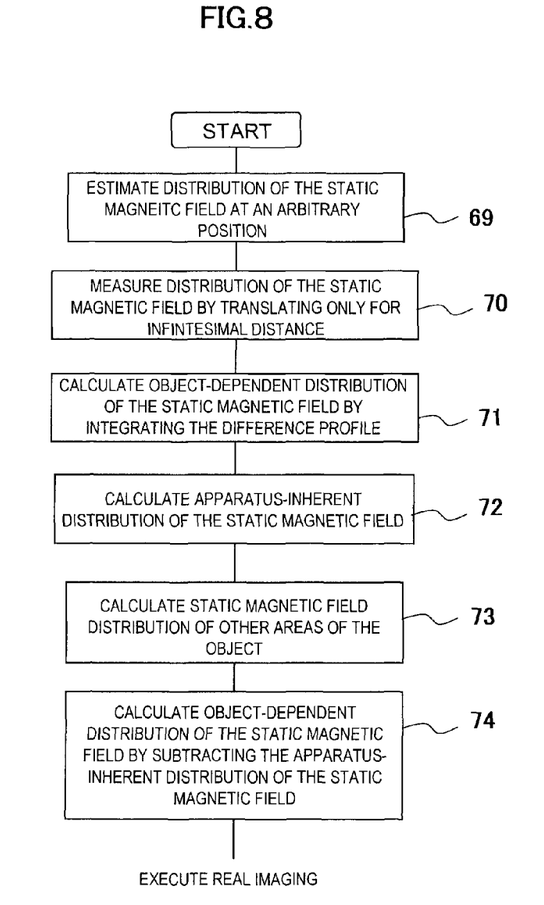
FIG. 8 is a flow chart of the operation in the third embodiment of the MRI apparatus related to the present invention.
Figure 9:
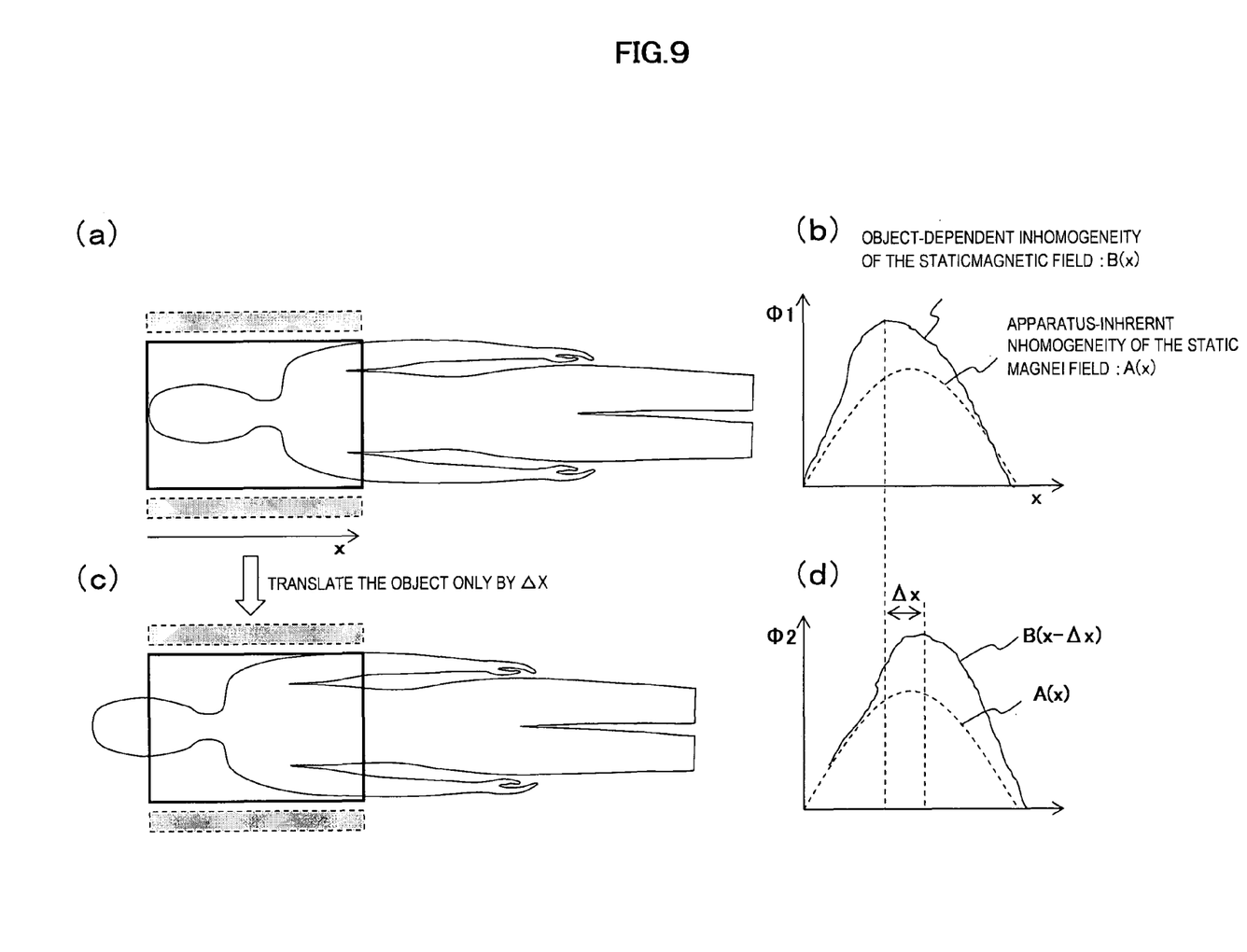
FIG. 9 is a schematic diagram of the shimming measurement in the third embodiment.

Next, concrete configuration of the MRI apparatus and method in embodiment 3 will be described. The imaging steps in the present embodiment are similar as the embodiments 1 and 2, and only the only difference is the steps for shimming measurement. In the present embodiment, in order to obtain the object-dependent inhomogeneous distribution of the static magnetic field and the apparatus-inherent inhomogeneous distribution of the static magnetic field, two inhomogeneous distributions of the static magnetic field that are obtained when the gantry is placed in two positions in the vicinity of the object are used. FIG. 8 is a flow chart showing the operation of the embodiment 3 of the MRI apparatus related to the present invention, and FIG. 9 is a schematic diagram of the shimming measurement in embodiment 3. The procedures thereof will be described below.

(Step 69)

First, static magnetic field distribution is measured at an arbitrary position as shown in FIG. 9(a) (for example, the position for imaging the utmost head-region side of the object: the initial table position in the case of imaging the object from the head-region to the feet-region). FIG. 9(b) is a disintegrated profile of the static magnetic field distribution in the table movement direction (x-direction) measured in the present step. In more concrete terms in accordance with the FIG. 9(b), inhomogeneous distribution of the static magnetic field $\phi1(x)$ measured in the present step is formed by the addition of the apparatus-inherent inhomogeneous distribution of the static magnetic field A(x) and the object-dependent inhomogeneous distribution of the static magnetic field B(x) which can be expressed by the formula below.

$$\phi1(x)=A(x)+B(x) \quad (1)$$

(Step 70)

Next, as shown in FIG. 9(c), the static magnetic field distribution is to be measured at the position that the table is moved by a small distance $\Delta x$ (for example, the position where the head-region of the object is protruded by a small distance from the gantry). The profile of the static magnetic field distribution in the table movement direction (x-direction) measured in the present step is as illustrated in FIG. 9(d). In accordance with FIG. 9(d), inhomogeneous distribution of the static magnetic field $\phi2(x)$ measured in the present step is formed by the addition of the apparatus-inherent inhomogeneous distribution of the static magnetic field and the object-dependent inhomogeneous distribution of the static magnetic field. In this step though, while the apparatus-inherent inhomogeneous distribution of the static magnetic field is A(x) which is the same as the step 69, the object-dependent inhomogeneous distribution of the static magnetic field becomes B(x−Δx) due to the amount that the object is shifted in the x-axis direction.

$$\phi2(x)=A(x)+B(x-\Delta x) \quad (2)$$

(Step 71)

In the present step, the object-dependent inhomogeneous distribution of the static magnetic field in the head-region of the object is calculated based on the static magnetic field distributions $\phi1(x)$ and $\phi2(x)$ obtained in the step 69 and the step 70. The calculation thereof will be described below.

First, the subtraction of φ2(x) from φ1(x) is performed.

$$\phi1(x) - \phi2(x) = B(x) - B(x - \Delta x) \quad (3)$$
$$= \Delta B(x)/\Delta X$$
$$= dB(x)/dx$$

In accordance with the above formula, the result of subtracting profile φ2(x) from profile φ1(x) turns out to be the derivative value of the object-dependent inhomogeneous distribution of the static magnetic field in the x-axis direction in the respective positions of the object. Therefore, the object-dependent inhomogeneous distribution of the static magnetic field in the respective positions of the object can be obtained by integrating the difference profile acquired by the formula (3) in the x-axis direction as expressed in the formula below.
[Formula 4]

$$\int_0^x dB(x)/dx \cdot dx = B(x) \quad (4)$$

(Step 72)
Next, the apparatus-inherent inhomogeneous distribution of the static magnetic field A(x) is to be obtained by subtracting object-dependent inhomogeneous distribution of the static magnetic field B(x) obtained using the formula (4) in the step 71 from φ1(x) which is on the left-hand side in the formula (1).
(Step 73)
Next, inhomogeneous distribution of the static magnetic field of the regions other than the head-region of the object is to be measured while moving the table step-wise or continuously. Then the object-dependent inhomogeneous distribution of the static magnetic field of the regions other than the head-region of the object (abdominal region, legs, etc.) B(x) is to be obtained by subtracting the apparatus-inherent inhomogeneous distribution of the static magnetic field A(x) acquired in the step 72 from the measured distribution.

To execute imaging using the apparatus-inherent inhomogeneous distribution of the static magnetic field and the object-dependent inhomogeneous distribution of the static magnetic field acquired in the steps 69~73 is the same as the embodiment 1 or embodiment 2. The present embodiment has an advantage that the apparatus-inherent inhomogeneous distribution of the static magnetic field can be obtained using an object without using the phantom. While only the x-axis coordinate in the table moving direction is expressed in the expression formula of the inhomogeneous distribution of the static magnetic field in the above-described steps 69~73 for the purpose of simplification, it is needles's to say that there are actual cases that the inhomogeneous distribution of the static magnetic field is obtained considering also the coordinate of other directions such as y-axis direction and z-axis direction.

The present invention is not intended to be limited to the above-described embodiments, and various changes may be made without departing from the scope of the invention. For example, while the case for setting an imaging cross-section in one slice of the coronal direction is described in the above embodiments, the present invention may also be applied to the case of setting it in a plurality of slices in the coronal direction. Also, it is needless to say that the present invention is applicable to the imaging methods for setting the imaging cross-section in axial direction.

The invention claimed is:
1. A magnetic resonance imaging apparatus comprising:
   static magnetic field generating means for generating a static magnetic field in an imaging space;
   measuring means for generating a high-frequency magnetic field and a gradient magnetic field in the imaging space and measuring a nuclear magnetic resonance signal generated from an object to be examined placed in the imaging space;
   signal processing means for reconstructing a magnetic resonance image based on the nuclear magnetic resonance signal;
   control means for controlling the measuring means and the signal processing means; and
   display means for displaying the magnetic resonance image obtained by the signal processing means,
   characterized in further comprising:
   storing means for storing a first set of information representing inhomogeneous distribution of the static magnetic field generated depending on the characteristic of the static magnetic field generating means and a second set of information representing inhomogeneous distribution of the static magnetic field generated depending on a tissue of the object;
   setting means for setting an imaging FOV in a desired region of the object;
   selecting means, from among the second set of information, for selecting the information corresponding to the set imaging FOV as a third set of information; and
   correcting magnetic field generating means for generating a correcting magnetic field for correcting the static magnetic field based on the third set of information and the first set of information.

2. The magnetic resonance imaging apparatus according to claim 1 comprising adding means for obtaining a fourth set of information by adding the third set of information and the first set of information, wherein the correcting magnetic field generating means generates the correcting magnetic field based on the fourth set of information.

3. The magnetic resonance imaging apparatus according to claim 1 characterized in comprising obtaining means for obtaining the first set of information and the second set of information.

4. The magnetic resonance imaging apparatus according to claim 3, wherein the obtaining means for obtaining the second set of information, comprises:
   means for measuring a fifth set of information representing inhomogeneous distribution of the static magnetic field generated when the object is placed in the imaging space; and
   subtracting means for subtracting the first set of information from the fifth set of information.

5. The magnetic resonance imaging apparatus according to claim 1 characterized in comprising moving means for moving the object in a static magnetic field.

6. The magnetic resonance imaging apparatus according to claim 5, wherein the control means changes generation amount of the correcting magnetic field in accordance with the movement of the object by the moving means.

7. The magnetic resonance imaging apparatus according to claim 6, wherein:
   the moving means moves the object step-wise; and
   the correcting magnetic field generating means changes the generation amount of the correcting magnetic field based on the fourth set of information which is added with respect to every step.

8. The magnetic resonance imaging apparatus according to claim 6, wherein:
  the moving means moves the object continuously; and
  the correcting magnetic field generating means generates the correcting magnetic field based on the fourth set of the information which is added with respect to every collection of more than at least one nuclear magnetic signal.

9. The magnetic resonance imaging apparatus according to claim 3, wherein the obtaining means comprises;
  derivative distribution calculating means for calculating a sixth set of information representing the distribution of spatial derivative value of the second set of information based on the difference information of the fifth set of information obtained in the case that the measurement is performed when the object is placed in adjacent two positions; and
  integral processing means for calculating the second set of information by integral processing of the sixth set of information obtained by the derivative distribution calculation means.

10. The magnetic resonance imaging apparatus according to claim 9, wherein the obtaining means comprises means for calculating the first set of information by subtracting the second set of information obtained by the integral processing means from the fifth set of information.

11. A magnetic resonance imaging method for obtaining a nuclear magnetic resonance image of an object to be examined placed in a static magnetic field, said method comprising:
  (1) storing a first set of information representing inhomogeneous distribution of the static magnetic field and a second set of information representing inhomogeneous distribution of the static magnetic field generated depending on a tissue of the object;
  (2) a step for setting an imaging FOV for representing a desired region of the object;
  (3) a step, from among the second set of information, for selecting the information corresponding to the set imaging FOV as a third set of information;
  (4) a step for obtaining a fourth set of information by adding the third set of information and the first set of information; and
  (5) a step for generating a correcting magnetic field based on the fourth set of information, and measuring a nuclear magnetic field generated thereby.

12. The magnetic resonance imaging method according to claim 11, further comprising:
  a step for measuring the first set of the information.

13. The magnetic resonance imaging method according to claim 12, further comprising:
  a step for measuring the second set of information.

14. The magnetic resonance imaging method according to claim 13, further comprising:
  a step for measuring the fifth set of information in the case that the table to which the object is placed is arranged in more than at least one position; and
  a step for calculating the second set of information by subtracting the first set of information from the fifth set of information.

15. The magnetic resonance imaging method according to claim 11, wherein:
  the measurement of the nuclear magnetic resonance signal in (5) is executed while moving the object stepwise; and
  the fourth set of information is obtained in (4) by calculating with respect to imaging FOV of the respective positions of every step.

16. The magnetic resonance imaging method according to claim 11, wherein:
  the measurement of the nuclear magnetic resonance signal in (5) is executed while the object is moving continuously; and
  the fourth set of information is obtained in (4) by calculating with respect to every collection of more than at least one nuclear magnetic resonance signal.

17. The magnetic resonance imaging method according to claim 16, wherein the calculation with respect to every collection of more than at least one nuclear magnetic resonance signal means the calculation with respect to every one cycle of echo signal acquisition of an overall phase encode.

18. The magnetic resonance imaging method according to claim 17, characterized in that the echo signal wherein the phase encode is zero at the central timing is measured in echo signal acquisition for each cycle.

19. The magnetic resonance imaging method according to claim 13, further comprising:
  (9) a step for calculating a sixth set of information representing the spatial derivative value of the second set of information based on the difference information of the two fifth sets of information obtained upon measurement when the object is placed in two adjacent positions; and
  (10) a step for calculating the second set of information by integral processing of the sixth set of information obtained in (9).

20. The magnetic resonance imaging method according to claim 19, further comprising:
  (11) a step for subtracting the second set of information obtained in (10) from the fifth set of information.

* * * * *